(12) United States Patent
Pauker et al.

(10) Patent No.: US 6,286,555 B1
(45) Date of Patent: Sep. 11, 2001

(54) REINFORCED ROLL-BACK TUBE FOR USE WITH ENDOSCOPES AND THE LIKE

(75) Inventors: Robert Pauker, Kissing; Thomas Viebach, Pischertshofen; Fritz Pauker, Wiffertshausen/Friedberg; Gerhard Weiglhofer, Schwabhausen/Well, all of (DE)

(73) Assignee: STM Medizintechnik Starnberg GmbH (DE)

( * ) Notice: Subject to any disclaimer, the term of this patent is extended or adjusted under 35 U.S.C. 154(b) by 0 days.

(21) Appl. No.: 09/095,857

(22) Filed: Jun. 11, 1998

(30) Foreign Application Priority Data

Nov. 3, 1997 (DE) ................................. 197 48 500

(51) Int. Cl.$^7$ ........................................ F16L 11/08
(52) U.S. Cl. ..................... 138/109; 138/125; 138/126; 138/132; 138/172
(58) Field of Search ........................ 138/109, 123, 138/124, 125, 126, 129, 132, 172

(56) References Cited

U.S. PATENT DOCUMENTS

| | | | |
|---|---|---|---|
| 2,349,730 | * 5/1944 | Horning | 138/129 |
| 2,784,989 | * 3/1957 | Krupp | 138/130 |
| 2,907,351 | * 10/1959 | Rohrback et al. | 138/109 |
| 2,911,236 | * 11/1959 | Thibault | 138/130 |
| 3,037,798 | * 6/1962 | Cooper | 138/127 |
| 3,828,112 | * 8/1974 | Johansen et al. | 138/125 |
| 5,868,437 | * 2/1999 | Teague | 138/149 |

* cited by examiner

Primary Examiner—James Hook
(74) Attorney, Agent, or Firm—Graybeal Jackson Haley LLP

(57) ABSTRACT

The invention relates to a roll-back tube construction, preferably for use with a flexible endoscope shaft, with a silicone roll-back tube consisting of an inner tube section which at least at one turn-back area is turned back to form an outer tube section and is provided with a reinforcement. The reinforcement preferably consists of a nylon filament winding with a pitch of 0.2 to 2 mm about a silicone tube, which reinforcement is in turn surrounded by a silicone covering. The roll-back tube construction is designed in accordance with the type of tube which can be rolled back at both ends, where front and rear outer tube sections are connected at one end by a tube-guiding sleeve arranged between them, through which an inner tube section extends. The tube-guiding sleeve is used for mounting a roll-back tube drive.

30 Claims, 2 Drawing Sheets

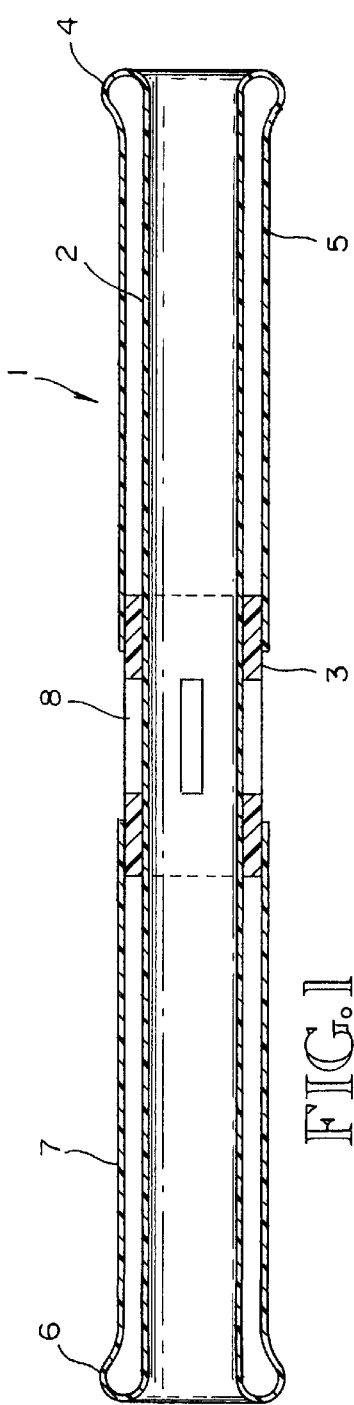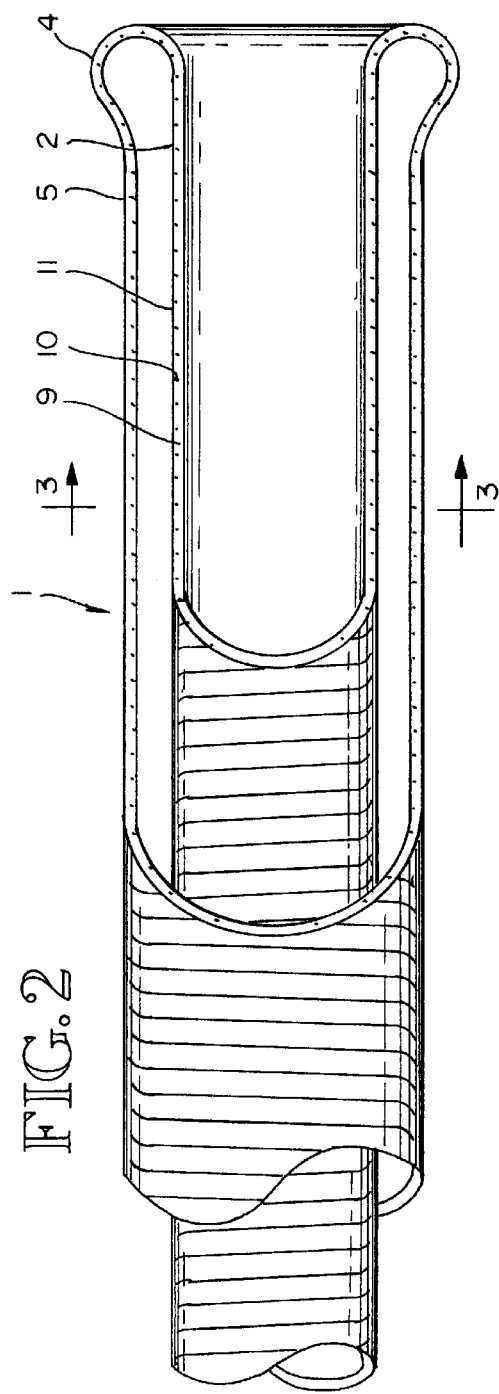

REINFORCED ROLL-BACK TUBE FOR USE WITH ENDOSCOPES AND THE LIKE

Figure 3:
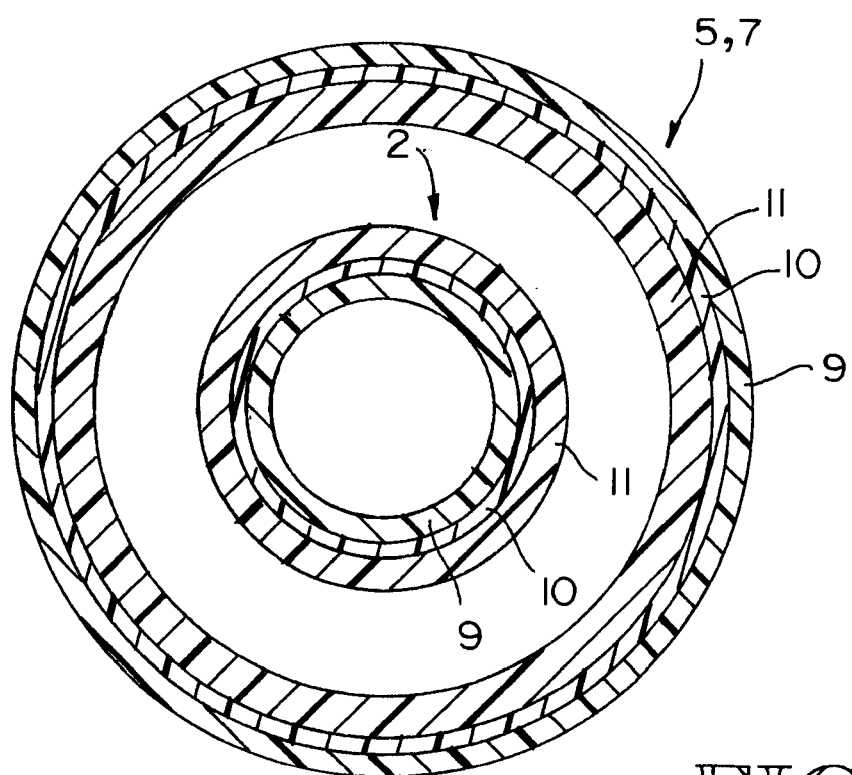

The present invention relates to a roll-back tube construction, preferably for an endoscopy apparatus, a catheter or another shaft-like circular appliance for examining channel-shaped cavities, for example in the human body, or for inserting operating instruments, medicaments, etc., and in particular a roll-back tube construction in accordance with the preamble of Patent claim 1.

Endoscopes are mainly used for visually examining the esophagus, the stomach, the intestine (from the mouth or from the anus), the urethra and the bladder. For this purpose, the endoscope is equipped at its distal end with a lighting device and with an optic, preferably a camera chip, which is connected via leads inside an endoscope shaft to a camera control means at the end of the endoscope shaft. The camera control means is in turn connected via a video processor to an external monitor on which an operating physician can identify the areas to be examined. The distal end of the shaft to be introduced into the cavity is here designed so that it can be bent in any direction, and it can be angled, much like a finger, manually by means of a handle, preferably via two control wheels with brake at the rear end section of the endoscope. In addition, the endoscope shaft generally has at least two channels passing through it, which open out at the distal end. When so required, these channels can be used for passing though cleaning fluid, for example, in order to clean an area which is to be examined, or $CO_2$ (air) for opening out the cavity or else various working instruments can be pushed through a working channel, for example forceps or scissors for removing tissue specimens, biopsy needles or heatable cutting wires, which can likewise be manually operated at the rear end of the endoscope shaft via operating wires or Bowden cables inside the inner channel.

The endoscope generally has an elongate tubular shape, with a diameter of about 9 to 15 mm, and consists of a bendable material so as to be able to follow the curvatures of the cavity which is to be examined, for example intestinal loops.

An endoscope of this generic type is known from the prior art, for example in accordance with DE 4,242,291 A1.

This endoscope essentially consists of an endoscope head or distal end, which is adjoined by an endoscope shaft consisting of a flexible bendable tubular body, and an operating mechanism at the rear end of the endoscope shaft. Moreover, in a rear end section of the endoscope there is provided a first drive or advance mechanism which exerts a driving force on the endoscope shaft via drive wheels. Arranged around the endoscope shaft, at least in its front section, there is a roll-back tube which is driven by a second drive or advance mechanism. The roll-back tube here consists of an inner tube section which bears slidably on the jacket surface of the endoscope shaft and is turned back in the area of the distal end of the endoscope to form a front outer tube section. The front outer tube section is also guided back as far as a second drive mechanism and fixed to the housing thereof. In the rear area of the endoscope, the inner tube section is turned back to form a rear outer tube section, which is likewise guided back to the second drive mechanism and fixed to the housing thereof, on the axial end side of the housing opposite the front outer tube section.

The second drive mechanism here acts on the inner roll-back tube section in order to move the latter in the axial direction of the endoscope shaft. For this purpose, the second drive mechanism has a type of cuff or collar which can be contracted in the radial direction and thus pressed with friction onto the inner tube section and can also be moved in the axial direction of the endoscope in the manner of a piston. In a further variant of this second drive mechanism, there are a number of friction wheels which bear on the inner tube section and thus exert an essentially continuous advance movement on the inner tube section. The radially acting pressing forces of the cuff or of the friction wheels of the second drive mechanism are here chosen to be so great that at least some of the applied pressing forces are transmitted, by a material deformation of the inner tube section, to the jacket surface of the endoscope shaft, so that the endoscope shaft is driven forwards together with the inner tube section despite the relative slidability.

Since, with this type of drive alone, effected by the second drive mechanism, i.e. without the first drive mechanism, the speed of advance of the roll-back tube at its front roll-back area would, because of its roll-back movement, be only half as great as that of the endoscope shaft, i.e. the endoscope shaft would, with increasing depth of penetration, emerge telescopically from the roll-back tube into the cavity, the first drive mechanism, mentioned in the introduction, exerts a braking force on the endoscope shaft, which braking force counteracts the advancing force of the second drive mechanism.

The second drive mechanism is in this case synchronized with the first drive mechanism in such a way that, in the interaction of the two drive mechanisms, the speed of movement of the inner tube section in an axial direction is approximately twice as great as the speed of movement of the endoscope shaft, this sliding relative to the inner endoscope shaft (i.e. the distal end of the endoscope shaft moves at the same speed as the front turn-back area of the roll-back tube).

In order to facilitate the relative movement between the endoscope shaft and the roll-back tube, the prior art according to DE 4,242,291 A1 further provides a lubricating device by means of which a lubricant can be forced into a gap between the inner tube section and the endoscope shaft and also into a cavity between the inner and outer tube section. For this purpose, the lubricating device has, inter alia, a cone-shaped sleeve which is slipped over the endoscope shaft and interacts sealingly with the rear roll-back area of the roll-back tube, which rides up onto the cone-shaped sleeve. The lubricant, which is forced by means of a pump into a gap between the cone-shaped sleeve and the endoscope shaft, spreads out between the inner tube section and the endoscope shaft along the entire length of the roll-back tube, and excess amounts of lubricant in the front turn-back area of the roll-back tube emerge into the cavity which is to be examined.

According to an inhouse prior art, the inventor also has in development an endoscopy apparatus which uses a double roll-back tube system of the above generic type, as is described in brief hereinbelow:

This endoscopy apparatus has an endoscope shaft which is guided slidably in a tube which is rolled back at both ends and which can once again be moved by a drive mechanism which acts on the inner tube section of the roll-back tube. The drive mechanism has at least one continuous advancing means, in particular friction wheels, which can press radially on the inner tube section in order to move the latter essentially continuously in the axial direction of the shaft. The great advantage of this is that the continuous advance of the roll-back tube system can be exactly controlled and thus, for example, the distal end of the endoscope can be guided to the exact location.

It is provided here that the pressing force of the advancing means on the inner tube section is chosen such that the shaft is in direct frictional contact with the inner tube section, at least in the area of the advancing means. The advancing means is made up of one or more friction wheels which are prestressed against the inner tube section with a predetermined or adjustable pressing force, so that it is possible to ensure that the endoscope shaft is advanced into the cavity to be examined within a patient in a movement which is on the one hand continuous and on the other hand as slip-free as possible.

In addition, the drive mechanism has a device for synchronizing the shaft movement with the movement of the roll-back tube. This can be a rear and front end-piece or clamping piece which is fixed axially on the shaft, and on which the rear or front roll-back area of the roll-back tube bears firmly and slidingly, depending on the direction of advance, so that the roll-back tube, via the rear or front end-piece, applies a braking force to the endoscope shaft counter to the already prevailing advancing force of the advancing means.

Tests which the inventor has carried out in the meantime have shown, however, that in the case of an endoscopy apparatus configured in this way, and having the above-described roll-back tube system, the advancing forces which can be applied via the friction wheels are limited. The reason for this is that, on the one hand, the advancing forces of the friction wheels can only be partly transmitted via the inner tube section to the endoscope shaft because a film of lubricant builds up between the inner tube section and the jacket surface, which film allows a relative sliding movement between the endoscope shaft and the inner tube section. That is to say, another portion of the advancing force of the friction wheels acts on the front end-piece via the inner tube section, which front end-piece is in turn clamped on the endoscope shaft. On the other hand, the total braking forces, which arise at the rear end-piece or clamping piece of the endoscope shaft counter to the advancing force of the friction wheels, act on the inner and outer, rear tube section of the roll-back tube.

The above-described roll-back tube essentially consists of silicone or a similar material and is of a thickness which permits as loss-free as possible a turning-back at the front and rear turn-back areas during a movement of the endoscope shaft. However, this construction only permits relatively slight shear loads, in particular on the inner tube section, in the advance direction of the endoscope shaft by the friction wheels or by the rear and front clamping piece, in which case, if a maximum permitted load limit, dependent on the material and its thickness, is exceeded, creasing occurs, especially of the inner tube section. In this state, not only is the relative slidability impaired, but the maximum advancing force which can be applied to the endoscope shaft is also reduced, so that the advancing movement slows down or even stops.

As a result of these tests, it may be stated that in the case of a roll-back tube construction according to the above description, the depth of penetration of the endoscope into the cavity to be examined is limited because, as the depth of penetration increases, an increasing advancing force must be applied to the endoscope shaft, which force is in turn limited by the maximum loadability, in particular of the inner tube section of the roll-back tube.

In view of these problems, the object of the present invention is to make available a roll-back tube construction by means of which an increased advancing force can be transmitted to an endoscope shaft, a catheter or a similar shaft-like circular appliance.

According to the invention, this object is achieved by means of a roll-back tube construction having the features according to claim 1.

Accordingly, the roll-back tube construction has a roll-back tube consisting of an inner tube section which, at least at a front turn-back area, is turned back to form an outer tube section, and the roll-back tube is provided with a reinforcement. This reinforcement prevents premature creasing of the roll-back tube, as a result of which an at least 3 times greater advancing force can be transmitted via the roll-back tube.

It is advantageous here if the reinforcement consists of a winding which is formed by a filament or spun filament, preferably of nylon. It is important here for the reinforcement to permit a slight elastic expansion of the tube, in particular for assembly purposes, which expansion is made possible by the nylon material used, because of its inherent elasticity. Alternatively, of course, a material with low inherent elasticity can also be used, such as, for example, a wire made of metal. In this case, however, the wire is not run straight, but in a loop formation or zigzag formation, in order to permit a certain extension and thus widening of the tube.

According to claim 4, the winding here has a pitch of 0.2 to 2 mm. By means of this design of the reinforcement, the roll-back behaviour, at at least the one, front turn-back area, is increased only insignificantly as a result of the milling of the tube material, so that the properties of the roll-back tube in terms of handling, arching at the front turn-back area, flexibility, etc, remain almost unchanged compared to a roll-back tube without reinforcement. Of course, the pitch does not need to be constant along the entire length of the tube, but can change as a function of the roll-back tube length. Thus, the pitch in the rear area, in which the force to be transmitted is at its greatest, can be small, and it can then increase continuously or in stages in the direction of the front area of the roll-back tube. In addition, the sphere of application of the roll-back tube construction according to the invention is not necessarily limited to shaft-like circular appliances, such as endoscope shafts, catheters, operating instruments etc. It is also conceivable, for example, to use the roll-back tube construction according to the invention to bring, for example, a medicament in tablet form or ampoule form to a specific location within a cavity and to leave it in position there. Nor is the roll-back tube construction restricted to medical applications, but can be used in all those situations in industry, research or manufacture in which channel-shaped cavities, shafts and conduits need to be examined or treated, and into which it is not possible to introduce conventional devices or instruments.

Further advantageous embodiments of the invention are here the subject matter of the subclaims.

The invention is discussed in greater detail hereinafter on the basis of a preferred illustrative embodiment and with reference to the attached drawings, in which:

FIG. 1 shows a longitudinal cutaway of a roll-back tube construction according to a preferred illustrative embodiment of the present invention, for use in particular in an endoscopy apparatus or a catheter, FIG. 2 shows a perspective view of an outer end section of the roll-back tube construction according to the preferred illustrative embodiment, and FIG. 3 shows a cross-section through the roll-back tube construction according to the invention.

As can be seen from FIG. 1, the roll-back tube construction according to the invention comprises a roll-back tube 1 consisting of an inner tube section 2 which is slidably guided through a drive and guide sleeve or tube-guiding part 3, with an annular gap forming between them, and is turned back in its front area (turn-back area) 4 to form a front outer tube section 5. The front outer tube section 5 is in this case brought back to the drive and guide sleeve (tube-guiding part) 3, which is made of a rigid material, preferably a synthetic material or a metal, and is fastened at an axial end section on the drive sleeve 3 in such a way that the latter comes to lie between the inner tube section 2 and front, outer tube section 5. That is to say, in other words, the end of the front, outer tube section 5 is preferably bonded or vulcanized onto the outer jacket surface of the drive sleeve 3 in an axial end area thereof. Alternatively, another type of fixing can be provided, for example a tube clamp or the like.

In a rear area (turn-back area) 6 of the roll-back tube 1, the inner tube section 2 is turned back to form a rear outer tube section 7 which is likewise brought back to the drive sleeve 3 and is fixed on an axial end of the drive sleeve 3 in the same way as has been described above. This axial end of the drive sleeve 3 likewise comes to lie between the inner and outer, rear tube sections 2 and 7. The drive sleeve 3 is used, on the one hand, as a guiding element for the inner tube section 2, in order to prevent warps and the formation of folds and creases, and, on the other hand, as a connection piece for the front outer tube section and the rear outer tube section 7, in which case a central area of the drive sleeve 3 remains exposed on its outer jacket surface, i.e. remains uncovered by the roll-back tube 1. In this central section the drive sleeve 3 has at least one opening 8, preferably a longitudinal slot of predetermined width extending in the axial direction. In the present case, four or more longitudinal slots 8 are provided, arranged at a uniform angular distance from each other, of which two diametrically opposite longitudinal slots are shown in FIG. 1. In addition, the drive sleeve 3 preferably has, on its inner side, a number of continuous longitudinal grooves (not detailed) which open out at the end faces of the drive sleeve 3 into cavities, which are formed between the inner tube section 2 and the outer tube sections 5, 7. These longitudinal grooves can be run either axially parallel or in a helical shape.

As can be seen in particular from FIG. 1, the material, i.e. the type of material and strength of material, of the roll-back tube 1 is chosen in such a way that a bead-shaped widening forms in each case at the front and rear roll-back area 4, 6 as a result of an accumulation of material at the turn-back.

The type of the material and the strength of the material in the preferred illustrative embodiment of the invention are described in detail below with reference to FIGS. 2 and 3.

The roll-back tube 1 according to the preferred illustrative embodiment is made of a silicone material extruded to form a tube 9, with a wall thickness of 0.5 to 1.5 mm, preferably 0.8 mm. This silicone tube is surrounded by a reinforcement arrangement 10, preferably made of nylon (hereinafter referred to as the nylon winding or else as the wire winding), which in turn is covered by a covering 11 of silicone. The wall thickness of the covering 11 is in this case 0.1 to 0.5 mm, preferably 0.2 mm. The stiffening arrangement 10 made of nylon is, as can be seen in particular from FIG. 2, a nylon filament, or a nylon spun to give a filament, which is wound in the axial direction of the silicone tube 1 about its jacket surface, with a pitch of 0.2 to 2 mm, preferably 0.5 mm, with a predetermined tensioning. The covering 11 of silicone in this case fills the gaps (spaces) between the individual nylon filaments of the reinforcement or of the nylon winding 10 and in so doing covers the reinforcement 10 completely on the outside. The above statements in relation to the dimensions of the roll-back tube and of the nylon winding refer to a roll-back tube construction particularly for medical purposes, for example for an endoscope shaft or a catheter. These can, however, differ, particularly if the roll-back tube construction is for examining and working in conduits or shafts which cannot be accessed, or can only be accessed with difficulty, in another way. In addition, nylon as the material is only given as a preferred illustrative embodiment, and it can readily be replaced by another material having similar properties. The properties of nylon can also be simulated by constructional measures, as set out in brief below.

As has already been pointed out at the start, the reinforcement 10 must permit a slight expansion of the tube, so that the latter can be fitted. The spun nylon filament which is used permits such a widening as a result of its inherent elasticity. If, for example, a wire winding is used, the wire must be run in a zigzag formation, for example, in order to be able to be slightly stretched elastically in the longitudinal direction of the wire.

To produce the above-described roll-back tube construction according to the preferred illustrative embodiment, the following procedure is followed:

To produce the roll-back tube 1 per se, the silicone tube 9 produced by extrusion is first drawn elastically onto a metal rod or another circular article (not detailed), the diameter of which essentially corresponds to the internal diameter of the silcone tube 9 or is slightly greater. Using a winding machine (not shown), the nylon filament or spun nylon filament 10 is then wound on, the winding machine being guided simultaneously around the silicone tube 9 at a continuous speed of axial movement and the silicone tube 9 being rotated. This produces a nylon filament winding as reinforcement on the silicone tube 9, with a pitch of the aforementioned 0.2 to 2 mm.

After the winding procedure has been completed, liquid silicone is applied radially and uniformly onto the jacket surface of the silicone tube 9 and onto the reinforcement 10, as a result of which the covering 11 of 0.1 to 0.5 mm wall thickness is formed. This covering does not need to have the same wall thickness at every point, but can vary in the longitudinal direction of the tube. After the silicone has hardened, the tube 9 is subjected to a vulcanization step in order to obtain a sufficient bonding of the silicone/nylon filament laminate.

The roll-back tube 1, formed in the above manner, is then shortened to a certain length of about 2 to 3 m, and is guided through the externally manufactured drive sleeve 3.

The roll-back tube 1 is thereafter turned back outwards at its axial ends (roll-back areas 4, 6) and guided back to the drive sleeve 3 to form the outer, front and rear tube sections 5, 7. Finally, as is shown in FIG. 1, the roll-back tube ends are bonded sealingly or otherwise fixed on the outer face of the drive sleeve 3, on the respective axial end sections thereof.

The drive sleeve 3 here serves for securing the drive mechanism (not detailed) whose housing is clamped on the drive sleeve 3 in such a way that the opposite ends of the roll-back tube 1, fixed on the drive sleeve 3, come to lie between the drive sleeve 3 and the drive mechanism and its housing almost in the manner of seals. This drive mechanism has friction wheels (likewise not shown) which, when the drive mechanism is secured on the drive sleeve 3, protrude through the slots 8 represented in FIG. 1. The endoscope shaft (likewise not shown) or a shaft-like circular article, such as, for example, a catheter, is finally introduced into the roll-back tube 1, its diameter being slightly smaller than the internal diameter of the inner tube section 2 of the roll-back tube 1, and the friction wheels press against the endoscope shaft (not shown) via the inner tube section 2.

Trials conducted by the inventor on an endoscopy apparatus have shown that, compared to a non-reinforced roll-back tube made exclusively of silicone or another material (e.g. neoprene), the roll-back tube 1 with the above-described nylon winding 10 in addition to the guide sleeve 3, or with the above-described constructional design of the roll-back tube 1, is able to transmit 3 times as much shearing force in the axial direction on the endoscope shaft before it shows a tendency to crease formation. The roll-back behaviour is influenced only slightly by the above-described nylon winding 10, so that loss of efficiency, i.e. an increase in the driving force required by the turn-back procedure during introduction of the endoscope, remains minimal.

Finally, it should be noted that the constructional design of the roll-back tube 1, in particular the design of the reinforcement 10 according to the invention, is not restricted to the roll-back tube of the type which is rolled back at both ends. The roll-back tube construction can also be advantageously used on roll-back tubes rolled back at one end, in which cases the rear turn-back area, which, according to the above description, takes up a braking force counter to the advancing force of the friction wheels for synchronizing the advance speeds of the endoscope shaft and of the roll-back tube, is replaced by a further driving and braking mechanism which acts exclusively on the endoscope shaft, independently of the actual driving device, and therefore only a turn-back in the front area of the roll-back tube is necessary for the advance movement of the endoscope shaft and of the roll-back tube.

Moreover, the invention is not limited to the exclusive use of silicone as the material for the tube; instead other materials having the same or similar properties in respect of processing, flow behaviour and elasticity, compatibility with the human body, reaction with lubricants, etc., can also be used as base material.

In summary, the invention thus relates to a roll-back tube construction as transporting means, preferably for a flexible endoscope shaft, with a silicone roll-back tube consisting of the inner tube section, which at least at one turn-back area is turned back to form the outer tube section, and which is provided with a reinforcement. The reinforcement consists of a nylon filament winding or a wire winding with a pitch of 0.2 to 2 mm about the silicone tube, which reinforcement is in turn surrounded by the silicone covering. The roll-back tube construction is designed in accordance with the type of tube which can be rolled back at both ends, where front and rear outer tube sections are connected at one end by means of a tube-guiding sleeve arranged between them, through which the inner tube section extends. The tube-guiding sleeve is used for mounting the roll-back tube drive.

What is claimed is:

1. An improvement for a roll-back tube construction for use with a flexible shaft, the construction having an inner tube section with at least one turn-back area that forms a portion of an outer tube section, the improvement comprising a reinforcement winding integral to the outer tube section, the at least one turn-back area and a portion of the inner tube section.

2. The construction of claim 1 wherein the winding is selected from the group consisting of a filament, a spun filament, and a wire.

3. The construction of claim 2 wherein the winding has a pitch substantially between 0.2 to 2 mm.

4. The construction of claim 2 wherein the winding has a pitch of about 0.5 mm.

5. The construction of claim 1 wherein the winding is elastic.

6. The construction of claim 1 wherein the winding has a pitch substantially between 0.2 to 2 mm.

7. The construction of claim 1 wherein the winding has a pitch of about 0.5 mm.

8. The construction of claim 1 wherein the roll-back tube comprises a first layer, a second layer, and the winding is disposed between the first layer of the roll-back tube and the second layer of the roll-back tube.

9. The construction of claim 8 wherein the first layer has sectional thickness substantially between 0.5 and 2.5 mm.

10. The construction of claim 8 wherein the second layer has sectional thickness substantially between 0.1 and 0.5 mm.

11. The construction of claim 8 wherein the first layer is an inner layer and the second layer is an outer layer.

12. The construction of claim 11 wherein the first layer and the second layer are formed from silicone.

13. The construction of claim 1 further comprising a tube-guiding sleeve having first and second axial ends through which the inner tube section runs wherein a first portion of the roll-back tube is fixed to the first axial end and a second portion of the roll-back tube is fixed to the second axial end.

14. The construction of claim 1 wherein the winding forms a zig-zag or loop pattern.

15. The construction of claim 1 wherein the pitch of winding differs in the longitudinal direction of the roll-back tube as a function of the roll-back tube length.

16. The construction of claim 1 wherein the tube has a generally constant average sectional thickness.

17. An improvement for a roll-back tube construction for use with a flexible shaft, the construction having a body portion, a first end, and a second end wherein at least the first end is axially turned back on itself so as to define an outer tube section that is substantially coaxial with the body portion and wherein the body portion forms an inner tube section, the improvement comprising:

a reinforcement winding selected from a group consisting of a filament, spun filament, and a wire, wherein the winding is integral to the first end, second end and body portion.

18. The construction of claim 17 wherein the winding has a pitch substantially between 0.2 to 2 mm.

19. The construction of claim 17 wherein the winding has a pitch of about 0.5 mm.

20. The construction of claim 17 wherein the roll-back tube comprises a first layer, a second layer, and the winding is disposed between the first layer of the roll-back tube and the second layer of the roll-back tube.

21. The construction of claim 20 wherein the first layer has sectional thickness substantially between 0.5 and 2.5 mm.

22. The construction of claim 20 wherein the second layer has sectional thickness substantially between 0.1 and 0.5 mm.

23. The construction of claim 20 wherein the first layer is an inner layer and the second layer is an outer layer.

24. The construction of claim 23 wherein the first layer and the second layer are formed from silicone.

25. The construction of claims 17 further comprising a tube-guiding sleeve having first and second axial ends through which the inner tube section runs wherein a first portion of the roll-back tube is fixed to the first axial end and a second portion of the roll-back tube is fixed to the second axial end.

26. An improvement for a roll-back tube construction for use with a flexible shaft, the construction having an inner tube section with at least one turn-back area that forms a portion of an outer tube section, the improvement comprising:

a winding selected from a group consisting of a filament, spun filament, and a wire, and integral to the at least one turn-back area, the outer tube section and a portion of the inner tube section, and disposed between a first layer of the roll-back tube and a second layer of the roll-back tube, and a tube-guiding sleeve having first and second axial ends through which the inner tube section runs wherein a first portion of the roll-back tube is fixed to the first axial end and a second portion of the roll-back tube is fixed to the second axial end.

27. The construction of claim 26 wherein the winding is elastic.

28. The construction of claim 26 wherein the winding has a pitch substantially between 0.2 and 2 mm.

29. The construction of claim 26 wherein the first layer is constructed from silicone and has a sectional thickness substantially between 0.5 and 2.5 mm and the second layer is constructed from silicone and has a sectional thickness substantially between 0.1 and 0.5 mm.

30. The construction of claim 26 wherein the winding is elastic, the winding has a pitch substantially between 0.2 and 2 mm, the first layer is constructed from silicone and has a sectional thickness substantially between 0.5 and 2.5 mm, and the second layer is constructed from silicone and has a sectional thickness substantially between 0.1 and 0.5 mm.

* * * * *